United States Patent
Hamada et al.

(10) Patent No.: US 12,408,892 B2
(45) Date of Patent: Sep. 9, 2025

(54) ACOUSTIC MATCHING LAYER MATERIAL, COMPOSITION FOR ACOUSTIC MATCHING LAYER MATERIAL, ACOUSTIC MATCHING SHEET, ACOUSTIC WAVE PROBE, ACOUSTIC WAVE MEASUREMENT APPARATUS, AND METHOD FOR MANUFACTURING ACOUSTIC WAVE PROBE

(71) Applicant: FUJIFILM Corporation, Tokyo (JP)

(72) Inventors: Kazuhiro Hamada, Ashigarakami-gun (JP); Yoshihiro Nakai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 925 days.

(21) Appl. No.: 17/646,518

(22) Filed: Dec. 30, 2021

(65) Prior Publication Data

US 2022/0125404 A1    Apr. 28, 2022

Related U.S. Application Data

(63) Continuation of application No. PCT/JP2020/030554, filed on Aug. 11, 2020.

(30) Foreign Application Priority Data

Aug. 30, 2019  (JP) ................. 2019-159043

(51) Int. Cl.
*A61B 8/00* (2006.01)
*B06B 1/06* (2006.01)
*G10K 11/02* (2006.01)

(52) U.S. Cl.
CPC ............ *A61B 8/4281* (2013.01); *B06B 1/067* (2013.01); *G10K 11/02* (2013.01); *B06B 2201/76* (2013.01)

(58) Field of Classification Search
CPC ............ G10K 11/02; C08K 3/08; C08L 63/00
See application file for complete search history.

(56) References Cited

U.S. PATENT DOCUMENTS

| 6,096,411 A * | 8/2000 | Nakatani ............ C08K 3/08 428/209 |
| 2002/0161301 A1 | 10/2002 | Venkataramani et al. |
| 2007/0205698 A1 | 9/2007 | Chaggares et al. |
| 2020/0118703 A1 * | 4/2020 | Hirata ............ B22F 1/102 |

FOREIGN PATENT DOCUMENTS

| CN | 105806509 A * | 7/2016 | ........ G01K 11/32 |
| DE | 43 13 229 A1 | 10/1994 | |
| JP | 2003-169397 A | 6/2003 | |

(Continued)

OTHER PUBLICATIONS

English Machine Translation of CN105806509B (Year: NONE).*

(Continued)

*Primary Examiner* — Randy P Gulakowski
*Assistant Examiner* — Holley Grace Hester
(74) *Attorney, Agent, or Firm* — Sughrue Mion, PLLC

(57) ABSTRACT

An acoustic matching layer material contains an epoxy resin component, a metal particle, and a ceramic particle, in which the acoustic matching layer material has an acoustic velocity of less than 3500 m/sec, and has an acoustic impedance of 18 Mrayl or more.

11 Claims, 1 Drawing Sheet

(56) References Cited

FOREIGN PATENT DOCUMENTS

| | | |
|---|---|---|
| JP | 2006-174992 A | 7/2006 |
| JP | 2009-515439 A | 4/2009 |
| JP | 2009-273835 A | 11/2009 |
| JP | 2013-192113 A | 9/2013 |
| JP | 2015-082764 A | 4/2015 |
| JP | 2017-060196 A | 3/2017 |
| WO | 2016/083808 A1 | 6/2016 |

OTHER PUBLICATIONS

Onda, Acoustic Properties of Solids (Year: 2003).*
NDT Systems, Common Material Velocities of Sound (Year: NONE).*
NDT Supply.com, Inc., Ultrasonic Reference Data (Year: NONE).*
International Preliminary Report on Patentability dated Mar. 1, 2022 in International Application No. PCT/JP2020/030554.
Written Opinion of the International Searching Authority dated Oct. 27, 2020 in International Application No. PCT/JP2020/030554.
International Search Report dated Oct. 27, 2020 in International Application No. PCT/JP2020/030554.
Chinese Office Action dated Oct. 11, 2023 in Application No. 202080050930.1.

\* cited by examiner

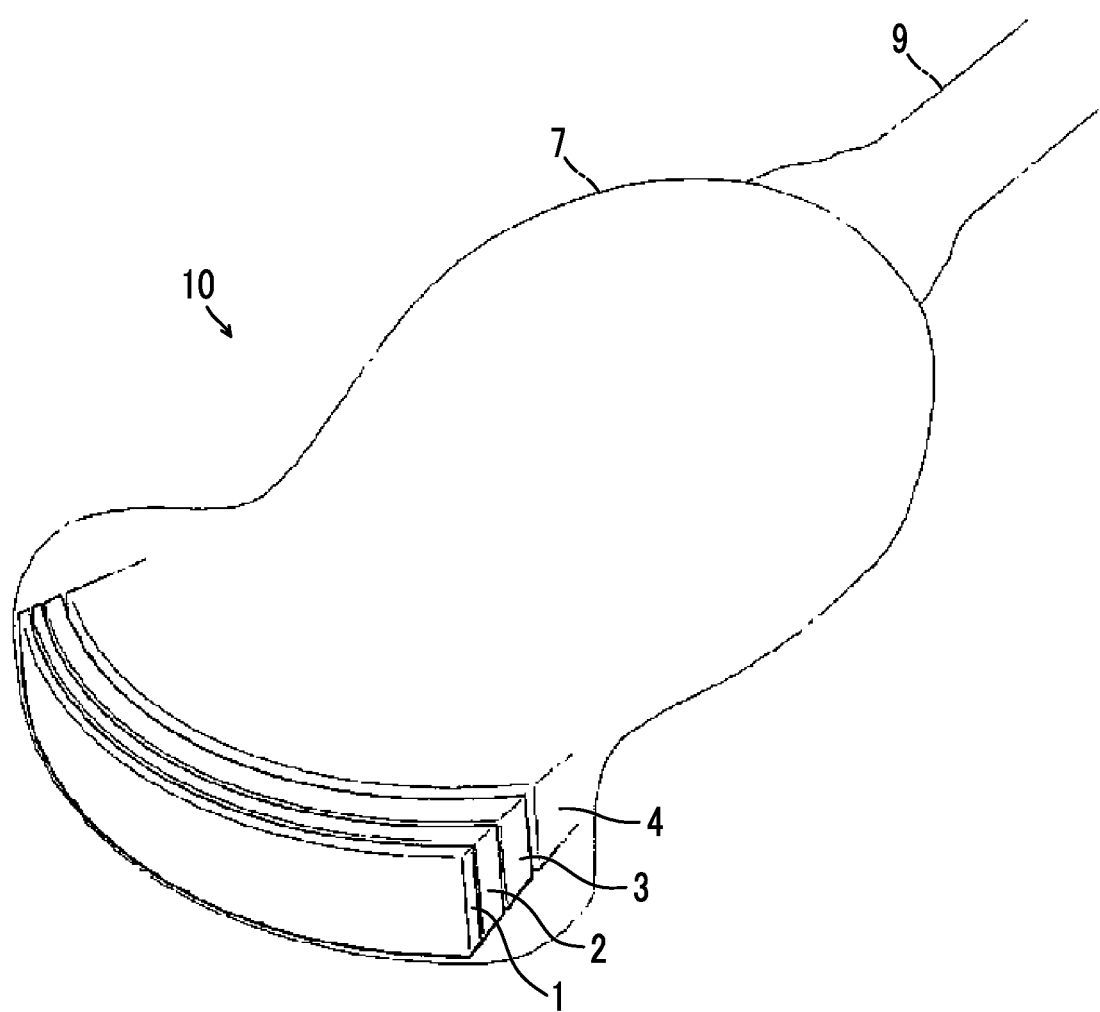

ACOUSTIC MATCHING LAYER MATERIAL, COMPOSITION FOR ACOUSTIC MATCHING LAYER MATERIAL, ACOUSTIC MATCHING SHEET, ACOUSTIC WAVE PROBE, ACOUSTIC WAVE MEASUREMENT APPARATUS, AND METHOD FOR MANUFACTURING ACOUSTIC WAVE PROBE

CROSS-REFERENCE TO RELATED APPLICATIONS

This application is a Continuation of PCT International Application No. PCT/JP2020/030554 filed on Aug. 11, 2020, which claims priority under 35 U.S.C § 119(a) to Japanese Patent Application No. 2019-159043 filed on Aug. 30, 2019. Each of the above application(s) is hereby expressly incorporated by reference, in its entirety, into the present application.

BACKGROUND OF THE INVENTION

1. Field of the Invention

The present invention relates to an acoustic matching layer material, a composition for an acoustic matching layer material, an acoustic matching sheet, an acoustic wave probe, an acoustic wave measurement apparatus, and a method for manufacturing an acoustic wave probe.

2. Description of the Related Art

In an acoustic wave measurement apparatus, an acoustic wave probe is used which irradiates a test object such as a living body with an acoustic wave, receives a reflected wave (echo) therefrom, and outputs a signal. The reflected wave received by this acoustic wave probe is converted into an electric signal which is then displayed as an image. Accordingly, using the acoustic wave probe makes it possible to visualize and observe the interior of the test object.

An ultrasonic wave, a photoacoustic wave, or the like is appropriately selected as the acoustic wave according to the test object and the measurement conditions.

For example, an ultrasound diagnostic apparatus, which is a kind of acoustic wave measurement apparatus, transmits an ultrasonic wave to the interior of a test object, receives the ultrasonic wave reflected by the tissues inside the test object, and displays the received ultrasonic wave as an image.

In addition, a photoacoustic wave measurement apparatus, which is a kind of acoustic wave measurement apparatus, receives an acoustic wave radiated from the interior of a test object due to a photoacoustic effect, and displays the received acoustic wave as an image. The photoacoustic effect is a phenomenon in which an acoustic wave (typically an ultrasonic wave) is generated through thermal expansion after a test object absorbs an electromagnetic wave to generate heat in a case where the test object is irradiated with an electromagnetic wave pulse of visible light, near infrared light, microwave, or the like.

Since the acoustic wave measurement apparatus transmits and receives an acoustic wave to and from a test object, the acoustic wave probe is required to match the acoustic impedance with the test object (typically a human body). To satisfy this requirement, the acoustic wave probe is provided with an acoustic matching layer. This will be described by taking, as an example, a probe for an ultrasound diagnostic apparatus (also referred to as an ultrasound probe), which is a kind of acoustic wave probe.

The ultrasound probe includes a piezoelectric element that transmits and receives an ultrasonic wave and an acoustic lens that comes into contact with a living body, in which an acoustic matching layer is arranged between the piezoelectric element and the acoustic lens. An ultrasonic wave oscillated from the piezoelectric element is incident on a living body after being transmitted through the acoustic matching layer, further being transmitted through the acoustic lens. There is usually a difference in acoustic impedance (density×acoustic velocity) between the acoustic lens and the living body. In a case where this difference is large, the ultrasonic wave is easily reflected on the surface of the living body, and the incident efficiency of the ultrasonic wave into the living body is lowered. Therefore, the acoustic lens is required to have an acoustic impedance characteristic close to that of a living body.

On the other hand, the difference in acoustic impedance between the piezoelectric element and the living body is generally large. Accordingly, the difference in acoustic impedance between the piezoelectric element and the acoustic lens is also usually large. Therefore, in a case of a laminated structure of the piezoelectric element and the acoustic lens, the ultrasonic wave emitted from the piezoelectric element is reflected on the surface of the acoustic lens, and therefore the incident efficiency of the ultrasonic wave into the living body is lowered. In order to suppress this reflection of the ultrasonic wave, the above-mentioned acoustic matching layer is provided between the piezoelectric element and the acoustic lens. The acoustic impedance of the acoustic matching layer takes a value between the acoustic impedance of the living body or the acoustic lens and the acoustic impedance of the piezoelectric element, which leads to improved propagation efficiency of an ultrasonic wave from the piezoelectric element to the living body. In addition, in recent years, the development of an acoustic matching layer with more efficient propagation of an ultrasonic wave has been underway by providing a gradient in acoustic impedance from the piezoelectric element side to the acoustic lens side, through a configuration of an acoustic matching layer having a multi-layer structure in which a plurality of acoustic matching sheets (sheet-like acoustic matching layer materials) are laminated.

The acoustic impedance of the acoustic matching layer can be adjusted by formulating a filler such as a metal particle in a material for forming the acoustic matching layer. For example, JP2003-169397A and JP2017-60196A describe that a sheet in which a metal, alumina, silicon carbide, and the like are dispersed in a resin such as an epoxy resin is used as an acoustic matching layer.

SUMMARY OF THE INVENTION

In the acoustic matching layer having a multi-layer structure, the above-mentioned gradient of the acoustic impedance is designed such that the closer it is to the piezoelectric element, the larger the acoustic impedance of the acoustic matching sheet, and the closer it is to the acoustic lens, the smaller the acoustic impedance of the acoustic matching sheet. That is, an acoustic matching sheet having acoustic impedance close to the acoustic impedance of the piezoelectric element (usually about 25 Mrayl) is required on the piezoelectric element side; and an acoustic matching sheet having acoustic impedance close to the acoustic impedance of the living body (1.4 to 1.7 Mrayl in the human body) is required on the acoustic lens side. From the viewpoint of making the gradient of the acoustic impedance smoother, it is required to increase the number of laminated acoustic matching sheets having different acoustic impedances. In this case, each acoustic matching sheet is required to be thinner.

The acoustic impedance of the acoustic matching sheet is determined by multiplying a density and an acoustic velocity of a sheet constituent material. Therefore, in a case of trying to increase the acoustic impedance of the acoustic matching sheet used on the piezoelectric element side, it is conceivable to use a material having a high density and a high acoustic velocity. A metal material can be mentioned as a material satisfying this condition. However, in a case where the metal material is used as it is as the acoustic matching sheet, the acoustic velocity is too fast, consequently the acoustic wave also has a long wavelength (wavelength=acoustic velocity/frequency), which limits the thinning of the sheet.

In addition, there is a problem in terms of limited ductility of a metal in a case of processing a metal material into a sheet, and there is also a problem in terms of workability in a case where the metal material is used as it is as the acoustic matching sheet.

Therefore, as described above, the acoustic impedance is adjusted by dispersing metal particles in a resin (for example, JP2003-169397A and JP2017-60196A). However, as studied by the present inventors, in a form in which the metal particles are formulated in the resin, it has been found that (I) an increase in the formulation amount of the metal particles causes a significant decrease in the acoustic velocity, and in order to achieve the desired high acoustic impedance, it is necessary to use the metal particles in a considerably high formulation amount, and (II) in a case where the metal particles are used in such a high formulation amount, it is difficult to uniformly disperse the metal particles in the resin. In a case where the dispersion of the metal particles in the resin is non-uniform, the variation in in-plane acoustic wave characteristics of the acoustic matching sheet becomes large.

An object of the present invention is to provide an acoustic matching layer material capable of forming an acoustic matching sheet that has little variation in acoustic wave characteristics within a layer, exhibits an appropriately high acoustic velocity, is thin, and exhibits a high acoustic impedance, and a composition for an acoustic matching layer material suitable for preparing such an acoustic matching layer material.

Another object of the present invention is to provide an acoustic matching sheet that has little variation in acoustic wave characteristics in a sheet, exhibits an appropriately high acoustic velocity, is thin, and exhibits a high acoustic impedance.

Another object of the present invention is to provide an acoustic wave probe formed of the acoustic matching sheet, and an acoustic wave measurement apparatus formed of the acoustic wave probe.

Another object of the present invention is to provide a method for manufacturing an acoustic wave probe formed of the acoustic matching layer material.

As a result of further studies in view of the above problems, the present inventors have found that, in a case where an epoxy resin before curing is mixed with a large amount of metal particles, the dispersibility of the metal particles in the epoxy resin can be effectively increased by using a planetary centrifugal mixer instead of a commonly used kneader, mixer, or the like; and by replacing a part of the metal particles with ceramic particles, the sheet (layer material) obtained by curing the epoxy resin can appropriately increase the acoustic velocity while enjoying an advantage of high density due to the metal particles, and therefore it is possible to achieve a desired thin-film acoustic matching sheet exhibiting a sufficiently high acoustic impedance. The present invention has been further studied and completed based on these findings.

That is, the foregoing objects of the present invention have been achieved by the following means.

<1>
An acoustic matching layer material containing an epoxy resin component, a metal particle, and a ceramic particle, having an acoustic velocity of less than 3,500 m/sec and an acoustic impedance of 18 Mrayl or more.

<2>
The acoustic matching layer material according to <1>, further containing a curing agent component.

<3>
The acoustic matching layer material according to <1> or <2>, in which the epoxy resin component contains at least one of a bisphenol A type epoxy resin component or a bisphenol F type epoxy resin component.

<4>
The acoustic matching layer material according to <2>, in which the curing agent component contains at least one of a primary amine component or a secondary amine component.

<5>
The acoustic matching layer material according to any one of <1> to <4>, in which the metal particle contains at least one metal of Groups 4 to 12 of the periodic table.

<6>
The acoustic matching layer material according to any one of <1> to <5>, in which the metal particle has a specific gravity of 9 or more.

<7>
The acoustic matching layer material according to any one of <1> to <6>, in which the ceramic particle contains at least one atom of Groups 1 to 3 or 13 to 17 of the periodic table.

<8>
The acoustic matching layer material according to any one of <1> to <7>, in which the ceramic particle contains at least one of Mg, Ca, Ba, B, Al, Y, or Si and at least one of O, C, N, or S.

<9>
The acoustic matching layer material according to any one of <1> to <8>, in which the ceramic particle contains at least one of cordierite, boron carbide, silicon carbide, alumina, aluminum nitride, magnesium oxide, silicon nitride, boron nitride, or yttrium oxide.

<10>
A composition for manufacturing the acoustic matching layer material according to any one of <1> to <9>, containing the epoxy resin, the metal particle, and the ceramic particle.

<11>
An acoustic matching sheet including the acoustic matching layer material according to any one of <1> to <9>.

<12>
An acoustic wave probe having the acoustic matching sheet according to <11> as an acoustic matching layer.

<13>
An acoustic wave measurement apparatus including the acoustic wave probe according to <12>.

<14>

The acoustic wave measurement apparatus according to <13>, in which the acoustic wave measurement apparatus is an ultrasound diagnostic apparatus.

<15>

A method for manufacturing the acoustic matching layer material according to any one of <1> to <9>, including stirring a composition containing the epoxy resin, the metal particle, and the ceramic particle with a planetary centrifugal mixer.

<16>

A method for manufacturing an acoustic wave probe, including forming an acoustic matching layer using the acoustic matching layer material according to any one of <1> to <9>.

In the description of the present invention, the expression "to" is used to mean that numerical values described before and after "to" are included as a lower limit value and an upper limit value, respectively.

The acoustic matching layer material according to an aspect of the present invention is capable of forming an acoustic matching sheet that has little variation in acoustic wave characteristics within a layer, exhibits an appropriately high acoustic velocity, is thin, and exhibits a high acoustic impedance.

The composition for an acoustic matching layer material according to the aspect of the present invention makes it possible to obtain the acoustic matching layer material by curing the same.

The acoustic matching sheet according to the aspect of the present invention has little variation in acoustic wave characteristics in a sheet, exhibits an appropriately high acoustic velocity, is thin, and exhibits a high acoustic impedance.

In addition, the acoustic wave probe according to the aspect of the present invention has the above-mentioned acoustic matching sheet.

The acoustic wave measurement apparatus according to the aspect of the present invention has an acoustic wave probe.

In addition, according to the method for manufacturing an acoustic wave probe according to the aspect of the present invention, an acoustic wave probe formed of the above-mentioned acoustic matching layer material can be obtained.

BRIEF DESCRIPTION OF THE DRAWINGS

FIG. 1 is a perspective view of an example of a convex type ultrasound probe which is an aspect of an acoustic wave probe.

DESCRIPTION OF THE PREFERRED EMBODIMENTS

[Acoustic Matching Layer Material]

The acoustic matching layer material according to the embodiment of the present invention (hereinafter, also simply referred to as "layer material according to the embodiment of the present invention") contains an epoxy resin component (a component derived from an epoxy resin), a metal particle, and a ceramic particle, and has an acoustic velocity (25° C.) of less than 3,500 m/sec and an acoustic impedance (25° C.) of 18 Mrayl or more.

The layer material according to the embodiment of the present invention is a material in which an epoxy resin component is used as a matrix and metal particles and ceramic particles are uniformly dispersed in the matrix. This uniformly dispersed state can be achieved by, for example, a specific stirring method which will be described later.

It is practical that the lower limit of the acoustic velocity is 2,000 m/sec. By setting the acoustic velocity to 2,000 m/sec or more, the acoustic impedance can be further increased while the acoustic matching sheet formed of the layer material is made into a thin film. The preferred lower limit of the acoustic velocity is 2,300 m/sec. The more preferred acoustic velocity is 2,300 m/sec or more and less than 2,750 m/sec.

It is practical that the upper limit of the acoustic impedance is 30 Mrayl.

The acoustic velocity and the acoustic impedance are determined by the method described in Examples which will be described later. In Examples, the measurement is carried out using a sheet having a thickness of 1 mm, but the measured values of acoustic velocity and density are substantially unaffected by the thickness. Therefore, the layer material can be appropriately processed into a sheet suitable for measurement, the acoustic velocity and density can be measured at three independent points in this sheet, and each arithmetic mean value can be obtained to determine the acoustic velocity and acoustic impedance of the layer material.

The shape of the layer material according to the embodiment of the present invention is not particularly limited, and examples thereof include a sheet shape, a columnar shape, and a prismatic shape, among which a sheet shape is preferable.

Hereinafter, the epoxy resin component may be referred to as a "binding material". In this situation, in a case where the layer material according to the embodiment of the present invention contains a curing agent component which will be described later, the epoxy resin component and the curing agent component are collectively referred to as a "binding material".

(Epoxy Resin)

An ordinary epoxy resin can be used as the epoxy resin for deriving the epoxy resin component contained in the layer material according to the embodiment of the present invention. For example, a bisphenol A type epoxy resin, a bisphenol F type epoxy resin, and a phenol novolac type epoxy resin are preferable. A bisphenol A type epoxy resin and a bisphenol F type epoxy resin are more preferable from the viewpoint of variation in acoustic wave characteristics.

The bisphenol A type epoxy resin used in the present invention is not particularly limited, and any bisphenol A type epoxy resin commonly used as a main agent of an epoxy-based adhesive can be widely used. Preferred specific examples of the bisphenol A type epoxy resin include bisphenol A diglycidyl ethers (jER825, jER828, and jER834 (all trade names), manufactured by Mitsubishi Chemical Corporation) and bisphenol A propoxylate diglycidyl ethers (manufactured by Sigma-Aldrich Co. LLC).

The bisphenol F type epoxy resin used in the present invention is not particularly limited, and any bisphenol F type epoxy resin commonly used as a main agent of an epoxy-based adhesive can be widely used. Preferred specific examples of the bisphenol F type epoxy resin include bisphenol F diglycidyl ether (trade name: EPICLON 830, manufactured by DIC Corporation) and 4,4'-methylenebis (N,N-diglycidylaniline).

The phenol novolac type epoxy resin used in the present invention is not particularly limited, and any phenol novolac type epoxy resin commonly used as a main agent of an epoxy-based adhesive can be widely used. Such a phenol novolac type epoxy resin is commercially available, for example, as product number 406775 (poly[(phenyl glycidyl ether)-co-formaldehyde]) from Sigma-Aldrich Co. LLC.

The epoxy resin may consist of the above-mentioned epoxy resin or may include, in addition to the above-mentioned epoxy resin, another epoxy resin (for example, an aliphatic epoxy resin) as long as the effects of the present invention are not impaired. The content of the three epoxy resins (total content of a bisphenol A type epoxy resin, a bisphenol F type epoxy resin, and a phenol novolac type epoxy resin) in the epoxy resin is preferably 80% by mass or more and more preferably 90% by mass or more.

The epoxy resin may be used alone or in combination of two or more thereof.

In the layer material according to the embodiment of the present invention, the epoxy resin component may be one in which an epoxy resin is cured alone, or one in which an epoxy resin is cured by reacting with a curing agent. That is, the layer material according to the embodiment of the present invention may contain a curing agent component (a component derived from the curing agent).

(Curing Agent)

One known as a curing agent for an epoxy resin can be used as the curing agent without particular limitation. Examples of the curing agent include an aliphatic amine, an aromatic amine, a dicyandiamide, a dihydrazide compound, an acid anhydride, and a phenol resin.

From the viewpoint of increasing the crosslink density and further reducing the variation in the acoustic characteristics of the obtained layer material, it is preferable to use at least one of a primary amine or a secondary amine. Above all, a compound having a primary amine and a secondary amine in one molecule is preferable, and specific examples thereof include a polyamide amine and a triethylene tetramine.

(Metal Particle)

The layer material according to the embodiment of the present invention contains a metal particle. By adjusting the content of the metal particle in the layer material, the density of the layer material can be adjusted, and the acoustic impedance of the layer material can be adjusted to a desired level. The metal particle may be surface-treated. This surface treatment can be carried out, for example, with reference to WO2019/088148A.

The metal constituting the metal particle is not particularly limited. The metal may be a metal atom alone or may be a carbide, a nitride, an oxide, or a boride of a metal. In addition, the metal may form an alloy. Examples of the alloy include high-tensile steel (Fe—C), chromium molybdenum steel (Fe—Cr—Mo), manganese molybdenum steel (Fe—Mn—Mo), stainless steel (Fe—Ni—Cr), 42 alloy, Invar (Fe—Ni), permendur (Fe—Co), silicon steel (Fe—Si), red brass, tombac (Cu—Zn), German silver (Cu—Zn—Ni), bronze (Cu—Sn), cupronickel (Cu—Ni), shakudo (Cu—Au), constantan (Cu—Ni), duralumin (Al—Cu), Hastelloy (Ni—Mo—Cr—Fe), Monel (Ni—Cu), Inconel (Ni—Cr—Fe), nichrome (Ni—Cr), ferromanganese (Mn—Fe), and cemented carbide (WC/Co).

The metal constituting the metal particle preferably contains at least one of the metals of Groups 4 to 12 of the periodic table.

In addition, from the viewpoint of lowering the acoustic velocity and increasing the acoustic impedance, the specific gravity (25° C., g/cm$^3$) of the metal constituting the metal particle is preferably 9 or more and more preferably 10 or more, and Mo and W are preferably used.

The particle diameter of the metal particle used in the present invention is preferably 0.01 to 100 μm and more preferably 1 to 10 μm, from the viewpoint of the viscosity of the composition for an acoustic matching layer material which will be described later and the variation in the acoustic wave characteristics of the acoustic matching layer material. Here, the "particle diameter" of the metal particle refers to an average primary particle diameter. In a case where the metal particle is surface-treated, it is preferable that the average primary particle diameter of the surface-treated metal particle is within the above range.

Here, the average primary particle diameter refers to a volume average particle diameter. The volume average particle diameter is determined as follows.

The metal particles are added to methanol in an amount of 0.5% by mass, followed by ultrasonication for 10 minutes to disperse the metal particles. The particle size distribution of the metal particles thus treated is measured by a laser diffraction/scattering-type particle size distribution analyzer (trade name: LA950V2, manufactured by HORIBA, Ltd.), and the volumetric median diameter of the measured metal particles is defined as the volume average particle diameter. The median diameter corresponds to a particle diameter at 50% in the particle size distribution represented in cumulative form.

(Ceramic Particle)

The ceramic particle used in the present invention is not particularly limited, and any ceramic particle commonly used as a filler for an acoustic matching layer material can be widely used.

The ceramic particle used in the present invention preferably contains at least one atom of Groups 1 to 3 or Groups 13 to 17 of the periodic table, and is more preferably a substance containing at least one of Mg, Ca, Ba, B, Al, Y, or Si (preferably one to three types thereof) and at least one of O, C, N, or S (preferably one type thereof).

The ceramic particle used in the present invention is preferably a carbide, a nitride, or an oxide containing at least one of Mg, Ba, B, Al, Y, or Si (preferably one to three types thereof), specific examples of which include magnesium-aluminum spinel (magnesium aluminate spinel, MgO·Al$_2$O$_3$), wollastonite (CaSiO$_3$), cordierite (2MgO·2Al$_2$O$_3$·5SiO$_2$), boron carbide (B$_4$C), silicon carbide (SiC), alumina (Al$_2$O$_3$), aluminum nitride (AlN), magnesium oxide (MgO), silicon nitride (Si$_3$N$_4$), boron nitride (BN), and yttrium oxide (Y$_2$O$_3$). From the viewpoint of lowering the acoustic velocity and increasing the acoustic impedance, it is preferable to use at least one of cordierite (2MgO·2Al$_2$O$_3$·5SiO$_2$), boron carbide (B$_4$C), silicon carbide (SiC), alumina (Al$_2$O$_3$), aluminum nitride (AlN), magnesium oxide (MgO), silicon nitride (Si$_3$N$_4$), boron nitride (BN), or yttrium oxide (Y$_2$O$_3$), and it is more preferable to use at least one of cordierite (2MgO·2Al$_2$O$_3$·5SiO$_2$), boron carbide (B$_4$C), silicon carbide (SiC), alumina (Al$_2$O$_3$), aluminum nitride (AlN), magnesium oxide (MgO), silicon nitride (Si$_3$N$_4$), or boron nitride (BN).

The particle diameter (average primary particle diameter) of the ceramic particle used in the present invention is preferably 0.01 to 100 μm and more preferably 1 to 15 μm, from the viewpoint of the viscosity of the composition for an acoustic matching layer material and the variation in the acoustic wave characteristics of the acoustic matching layer material. The particle diameter of the ceramic particle can be measured in the same manner as in the particle diameter of the metal particle.

The content of each of the binding material, the metal particle, and the ceramic particle in the layer material according to the embodiment of the present invention is appropriately adjusted according to the target acoustic velocity and acoustic impedance (the acoustic velocity is less than 3,500 m/sec, and the acoustic impedance is 18 Mrayl or more).

The content of the binding material in the layer material according to the embodiment of the present invention is preferably 1% to 10% by mass and more preferably 3% to 7% by mass. The content of the metal particle in the layer material according to the embodiment of the present invention is preferably 80% to 98% by mass, more preferably 85% to 95% by mass, still more preferably 86% to 93% by mass, and particularly preferably 87% to 92% by mass. The content of the ceramic particle in the layer material according to the embodiment of the present invention is preferably 1% to 18% by mass, more preferably 2% to 12% by mass, still more preferably 3% to 10% by mass, and particularly preferably 3% to 8% by mass.

The layer material according to the embodiment of the present invention may be composed of a binding material, a metal particle, and a ceramic particle. In addition, the layer material according to the embodiment of the present invention may contain components other than these components, as long as the effects of the present invention are not impaired. Examples of components other than the binding material and other than the metal particle and the ceramic particle (other components) include a curing retarder, a dispersant, a pigment, a dye, an antistatic agent, an antioxidant, a flame retardant, and a thermal conductivity improver.

The total content of the binding material, the metal particle, and the ceramic particle in the layer material according to the embodiment of the present invention is preferably 80% by mass or more and more preferably 90% by mass or more.

The layer material according to the embodiment of the present invention makes it possible to suppress variation in in-plane acoustic wave characteristics in a case of being formed into a sheet. For example, the standard deviation (Mrayl) of the in-plane acoustic impedance (Mrayl) in a case of being formed into a sheet is preferably less than 0.7 and more preferably less than 0.5. The lower limit of this standard deviation may be 0, and the standard deviation is usually 0.1 or more. This standard deviation is determined according to the method described in Examples which will be described later. Specifically, the layer material processed into a sheet is divided into three equal parts in a thickness direction, the acoustic impedances of three independent points are measured for each of the three obtained sheets, and the standard deviation is determined as a standard deviation of the acoustic impedance at a total of nine points. The thickness of the sheet has substantially no effect on the acoustic velocity and density.

<Composition for Acoustic Matching Layer Material>

The composition for an acoustic matching layer material according to the embodiment of the present invention (the composition used for the acoustic matching layer material according to the embodiment of the present invention, hereinafter also referred to as "the composition according to the embodiment of the present invention") contains an epoxy resin, a metal particle, and a ceramic particle.

In addition, the composition according to the embodiment of the present invention may contain the above-mentioned curing agent, or may contain the above-mentioned other components.

In a case where the composition according to the embodiment of the present invention contains an epoxy resin and a curing agent as a binding material, a curing reaction of the epoxy resin may proceed over time in the composition even under mild conditions. Therefore, the properties of this composition may change over time and thus may not be stable. However, for example, storing the above composition at a temperature of −10° C. or lower makes it possible to obtain a composition in a state in which each component is stably maintained without causing a curing reaction or with sufficient suppression of the curing reaction.

In addition, it is also preferable to form a material set for an acoustic matching layer in which a resin composition containing an epoxy resin and a metal particle is used as a main agent, and the main agent and a curing agent are separately separated. In a case of preparing an acoustic matching layer material, it is possible to prepare the acoustic matching layer material by mixing the main agent and the curing agent to prepare the composition according to the embodiment of the present invention, and subjecting this composition to a curing reaction.

The mass ratio of the epoxy resin and the curing agent constituting the binding material may be appropriately adjusted according to the type of the curing agent used and the like. For example, the epoxy resin/curing agent can be 99/1 to 20/80 and is preferably 90/10 to 40/60.

In addition, in a case where the composition according to the embodiment of the present invention is used by mixing the main agent and the curing agent at the time of preparing the layer material using the above-mentioned material set for an acoustic matching layer, it is preferably a configuration in which the main agent and the curing agent are mixed and used such that the mass ratio of the epoxy resin to the curing agent is epoxy resin/curing agent of 99/1 to 20/80; and it is more preferably a configuration in which the main agent and the curing agent are mixed and used such that the mass ratio of the epoxy resin to the curing agent is epoxy resin/curing agent of 90/10 to 40/60.

<Preparation of Composition for Acoustic Matching Layer Material>

The composition for an acoustic matching layer material according to the embodiment of the present invention can be obtained, for example, by mixing the components constituting the composition for an acoustic matching layer material. The mixing method is not particularly limited as long as each component can be substantially uniformly mixed, and for example, uniform mixing can be carried out by kneading the components using a planetary centrifugal mixer, which is preferable.

The planetary centrifugal mixer is a machine that mixes materials by material convection and shear stress due to centrifugal force generated by tilting a container containing materials and causing the container to rotate and revolve at high speed (movement of a planet around the sun, planetary motion).

In addition, in a case of making a material set for an acoustic matching layer containing a main agent consisting of a resin composition containing an epoxy resin, a metal particle, and a ceramic particle, and a curing agent for the epoxy resin, the main agent can be obtained by mixing the epoxy resin, the metal particle, and the ceramic particle. The composition for an acoustic matching layer material according to the embodiment of the present invention is obtained by mixing the main agent and the curing agent at the time of preparing the acoustic matching layer material. An acoustic matching layer material or a precursor thereof can be prepared by curing this composition while shaping it.

[Acoustic Matching Sheet (Acoustic Matching Layer)]

The layer material according to the embodiment of the present invention makes it possible to obtain an acoustic matching sheet by cutting or dicing the layer material to a desired thickness or shape, if necessary. In addition, the acoustic matching sheet can be further processed into a desired shape by a conventional method.

Specifically, for example, the composition according to the embodiment of the present invention is shaped into a desired sheet in a low temperature region where a curing reaction does not occur or in a low temperature region where a curing rate is sufficiently slow. Then, if necessary, a crosslinking structure is formed in the shaped product by heating or the like, followed by curing, and this shaped product is cut, diced, or the like to a desired thickness or shape as necessary to obtain an acoustic matching sheet or a precursor sheet thereof. That is, the acoustic matching sheet to be formed is preferably a cured substance obtained by curing the composition according to the embodiment of the present invention to form a three-dimensional network structure. This acoustic matching sheet is used as an acoustic matching layer of an acoustic wave probe. The configuration of the acoustic wave probe including the acoustic matching layer will be described later.

[Acoustic Wave Probe]

The acoustic wave probe according to the embodiment of the present invention has the acoustic matching sheet according to the embodiment of the present invention as at least one layer of an acoustic matching layer.

An example of the configuration of the acoustic wave probe according to the embodiment of the present invention is shown in FIG. 1. The acoustic wave probe shown in FIG. 1 is an ultrasound probe in an ultrasound diagnostic apparatus. The ultrasound probe is a probe which particularly uses an ultrasonic wave as an acoustic wave in an acoustic wave probe. For this reason, a basic structure of the ultrasound probe can be applied to the acoustic wave probe as it is.

<Ultrasound Probe>

An ultrasound probe 10 is a main component of the ultrasound diagnostic apparatus and has a function of generating an ultrasonic wave and transmitting and receiving an ultrasonic beam. The configuration of the ultrasound probe 10 is provided in the order of an acoustic lens 1, an acoustic matching layer 2, a piezoelectric element layer 3, and a backing material 4 from a distal end portion (the surface coming into contact with a living body which is a test object) as shown in FIG. 1. In recent years, an ultrasound probe having a laminated structure in which an ultrasonic transducer (piezoelectric element) for transmission and an ultrasonic transducer (piezoelectric element) for reception are formed of materials different from each other has been proposed in order to receive high-order harmonics.

(Piezoelectric Element Layer)

The piezoelectric element layer 3 is a portion which generates an ultrasonic wave and in which electrodes are attached to both sides of a piezoelectric element. In a case where a voltage is applied to the electrodes, the piezoelectric element layer generates an ultrasonic wave through repeated contraction and expansion of the piezoelectric element and through vibration.

A so-called ceramic inorganic piezoelectric body obtained by a polarization treatment of a single crystal such as crystallized quartz, $LiNbO_3$, $LiTaO_3$, or $KNbO_3$, a thin film such as ZnO or AlN, a $Pb(Zr, Ti)O_3$-based sintered body, or the like is widely used as the material constituting a piezoelectric element. In general, piezoelectric ceramics such as lead zirconate titanate (PZT) with good conversion efficiency are used.

In addition, wider bandwidth sensitivity is required for a piezoelectric element detecting a reception wave on a high frequency side. For this reason, an organic piezoelectric body has been used in which an organic polymer material such as polyvinylidene fluoride (PVDF) is used as the piezoelectric element suitable for a high frequency and a wide band.

Furthermore, cMUT using micro electro mechanical systems (MEMS) technology in which an array structure, which shows excellent short pulse characteristics, excellent wideband characteristics, and excellent mass productivity and has less characteristic variations, is obtained is disclosed in JP2011-071842A or the like.

In the present invention, it is possible to preferably use any piezoelectric element material.

(Backing Material)

The backing material 4 is provided on a rear surface of the piezoelectric element layer 3 and contributes to the improvement in distance resolution in an ultrasonic diagnostic image by shortening the pulse width of an ultrasonic wave through the suppression of excess vibration.

(Acoustic Matching Layer)

The acoustic matching layer 2 is provided in order to reduce the difference in acoustic impedance between the piezoelectric element layer 3 and a test object and to efficiently transmit and receive an ultrasonic wave.

(Acoustic Lens)

The acoustic lens 1 is provided to focus an ultrasonic wave in a slice direction by utilizing refraction to improve the resolution. In addition, it is necessary for the acoustic lens 1 to achieve matching of an ultrasonic wave with the acoustic impedance (1.4 to 1.7 Mrayl in a case of a human body) of a living body which is a test object after being closely attached to the living body and to reduce the amount of ultrasonic attenuation of the acoustic lens 1 itself.

That is, the sensitivity of transmission and reception of an ultrasonic wave is increased by using a material with acoustic velocity sufficiently lower than that of a human body, low ultrasonic attenuation, and acoustic impedance close to a value of the human skin, as the material for the acoustic lens 1.

The operation of the ultrasound probe 10 having such a configuration will be described. The piezoelectric element layer 3 is resonated after applying a voltage to the electrodes provided on both sides of a piezoelectric element, and an ultrasonic signal is transmitted to a test object from the acoustic lens. During reception of the ultrasonic signal, the piezoelectric element layer 3 is vibrated using the signal (echo signal) reflected from the test object and this vibration is electrically converted into a signal to obtain an image.

[Manufacturing of Acoustic Wave Probe]

The acoustic wave probe according to the embodiment of the present invention can be prepared by a conventional method, except that the acoustic matching sheet according to the embodiment of the present invention is used. That is, the method for manufacturing an acoustic wave probe according to the embodiment of the present invention includes a step of forming an acoustic matching layer on a piezoelectric element using the acoustic matching sheet according to the embodiment of the present invention. The piezoelectric element can be provided on the backing material by a conventional method.

In addition, an acoustic lens is formed on the acoustic matching layer by a conventional method using a material for forming the acoustic lens.

[Acoustic Wave Measurement Apparatus]

The acoustic wave measurement apparatus according to the embodiment of the present invention has the acoustic wave probe according to the embodiment of the present invention. The acoustic wave measurement apparatus has a function of displaying the signal intensity of a signal received by the acoustic wave probe and imaging the signal.

It is also preferable that the acoustic wave measurement apparatus according to the embodiment of the present invention is an ultrasonic measurement apparatus using an ultrasound probe.

EXAMPLES

The present invention will be described in more detail based on Examples in which an ultrasonic wave is used as an acoustic wave. The present invention is not limited to the ultrasonic wave, and any acoustic wave of an audible frequency may be used as long as an appropriate frequency is selected in accordance with a test object, measurement conditions, and the like. Hereinafter, the room temperature means 25° C.

Synthesis Example

<1> Preparation of Composition for Acoustic Matching Layer Material (1) Preparation of Composition for Acoustic Matching Layer Material Used in Example 1

90 parts by mass of metal particles (iron powder (Fe)) (EW-I, particle diameter: 2 μm, trade name, manufactured by BASF SE)), 5 parts by mass of ceramic particles (synthetic cordierite fine particle product SS-400, particle diameter: 4.5 μm, trade name, manufactured by Marusu Glaze Co., Ltd.), 4 parts by mass of an epoxy resin (bisphenol A diglycidyl ether ("jER825", trade name, manufactured by Mitsubishi Chemical Corporation, epoxy equivalent: 170)), and 1 part by mass of a curing agent (D-1) isophorone diamine (manufactured by FUJIFILM Wako Pure Chemical Corporation) were mixed by a planetary centrifugal mixer (trade name: ARV-310, manufactured by Thinky Corporation) to prepare a composition for an acoustic matching layer material which is used in Example 1.

(2) Preparation of Composition for Acoustic Matching Layer Material Used in Examples 2 to 33 and Comparative Examples 1 to 10

The composition for an acoustic matching layer material used in each of Examples 2 to 33 and Comparative Examples 1 to 10 was prepared in the same manner as in the preparation of the composition for an acoustic matching layer material used in Example 1, except that the composition was changed to the composition shown in Table 1 below.

(3) Preparation of Composition for Acoustic Matching Layer Material Used in Comparative Example 11

In a case where raw materials having the compositions shown in Table 1 below were tried to be mixed using a kneader (trade name: TDR100-3, manufactured by Toshin Co., Ltd.) under the conditions of 30° C. and 20 rpm, the blades did not rotate and the raw materials could not be mixed.

(4) Preparation of Composition for Acoustic Matching Layer Material Used in Comparative Example 12

In a case where raw materials having the compositions shown in Table 1 below were tried to be mixed using a pressurized kneader (trade name: TD0.3-3, manufactured by Toshin Co., Ltd.) under the conditions of 30° C. and 20 rpm, the blades did not rotate and the raw materials could not be mixed.

(5) Preparation of Composition for Acoustic Matching Layer Material Used in Comparative Example 13

In a case where raw materials having the compositions shown in Table 1 below were tried to be mixed using a Banbury mixer (trade name: BR600, manufactured by Toyo Seiki Seisaku-sho, Ltd.) under the conditions of 30° C. and 20 rpm, the blades did not rotate and the raw materials could not be mixed.

(6) Preparation of Composition for Acoustic Matching Layer Material Used in Comparative Example 14

The raw materials having the compositions shown in Table 1 below were mixed using a three roll mill (trade name: BR-100VIII, manufactured by AIMEX Co., Ltd.) under the condition of 83 rpm to prepare a composition for an acoustic matching layer material used in Comparative Example 14.

<2> Preparation of Acoustic Matching Layer Material (Acoustic Matching Sheet)

(1) Preparation of Acoustic Matching Sheet of Example 1

The composition for an acoustic matching layer material used in Example 1 was poured into a circular mold having a diameter of 40 mm and a depth of 3 mm, and cured at 80° C. for 18 hours and then at 150° C. for 1 hour to prepare a circular acoustic matching sheet having a diameter of 40 mm and a thickness of 3 mm. This sheet was cut into three circular acoustic matching sheets having a diameter of 40 mm and a thickness of 1 mm with a dicer, and one acoustic matching sheet (thickness: 1 mm) in the center was used for the following measurement.

(2) Preparation of Acoustic Matching Sheets of Examples 2 to 25 and 27 to 36, and Comparative Examples 1 to 10 and 14.

Acoustic matching sheets (thickness: 1 mm) were prepared in the same manner as in the acoustic matching sheet used in Example 1, except that the composition for an acoustic matching layer material used in each of Examples 2 to 25 and 27 to 36 and Comparative Examples 1 to 10 and 14 was used instead of the composition for an acoustic matching layer material used in Example 1. The thus-prepared acoustic matching sheets were used for the following measurement.

(3) Preparation of Acoustic Matching Sheet of Example 26

The composition for an acoustic matching layer material used in Example 33 was poured into a circular mold having a diameter of 40 mm and a depth of 3 mm, and cured at 150° C. for 1 hour to prepare a circular acoustic matching sheet having a diameter of 40 mm and a thickness of 3 mm. This sheet was cut into three circular acoustic matching sheets having a diameter of 40 mm and a thickness of 1 mm with a dicer, and one acoustic matching sheet (thickness: 1 mm) in the center was used for the following measurement.

[Test Example 1] Measurement of Acoustic Velocity

The ultrasonic velocity was measured at 25° C. using a sing-around acoustic velocity measurement apparatus (trade name: "UVM-2 model", manufactured by Ultrasonic Engineering Co., Ltd.) according to JIS Z2353 (2003). With respect to the circular acoustic matching sheet having a diameter of 40 mm and a thickness of 1 mm obtained above, for three circular regions having a diameter of 1.5 cm that do not overlap one another, the entire inside of these three circular regions (small probe size of a single channel) was measured. The arithmetic mean value of the acoustic velocity in the above three circular regions was calculated and evaluated by applying it to the following evaluation standards. A rating of A to C is acceptable in the present test. In a case where it is rated as D, it is necessary to make the sheet thick in order to function as an acoustic matching layer, which is not preferable in terms of acoustic wave attenuation and probe design. In a case where it is rated as B, both high acoustic impedance and thinning of the sheet can be achieved at a higher level, which is more preferable in practical use.

-Evaluation Standards-
A: The acoustic velocity is 2000 [m/sec] or more and less than 2300 [m/sec]
B: The acoustic velocity is 2300 [m/sec] or more and less than 2750 [m/sec]
C: The acoustic velocity is 2750 [m/sec] or more and less than 3500 [m/sec]
D: The acoustic velocity is 3500 [m/sec] or more

[Test Example 2] Density Measurement and Acoustic Impedance Calculation

With respect to the circular acoustic matching sheet having a diameter of 40 mm and a thickness of 1 mm obtained above, a test piece of 10 mm×10 mm was cut out from each of the three circular regions whose acoustic velocity was measured above. The density of each cut-out sample at 25° C. was measured using an electronic hydrometer (trade name: "SD-200L", manufactured by Alfa Mirage Co., Ltd.) in accordance with the density measurement method of Method A (underwater substitution method) described in JIS K7112 (1999), and the arithmetic mean value of the density in the three circular regions was obtained. The acoustic impedance was calculated from the product of the density obtained in this manner and the above-mentioned acoustic velocity (arithmetic mean value of density×arithmetic mean value of acoustic velocity), and evaluated by applying it to the following evaluation standards. A rating of A and B is acceptable in the present test.

-Evaluation Standards-
A: The acoustic impedance is 22 Mrayl or more
B: The acoustic impedance is 18 Mrayl or more and less than 22 Mrayl
C: The acoustic impedance is 15 Mrayl or more and less than 18 Mrayl
D: The acoustic impedance is less than 15 Mrayl

[Test Example 3] Variation in Acoustic Impedance (AI)

Three circular acoustic matching sheets having a diameter of 40 mm and a thickness of 1 mm cut out from the circular acoustic matching sheet having a diameter of 40 mm and a thickness of 3 mm obtained above were used. For each of the three sheets, the acoustic impedance was calculated for each of three circular regions having a diameter of 1.5 cm that do not overlap one another. For each of Examples and Comparative Examples, the standard deviations of nine acoustic impedances obtained from a total of nine circular regions were obtained, and the variations in acoustic characteristics were evaluated by applying them to the following evaluation standards. A rating of A and B is acceptable in the present test.

<Acoustic Velocity>
The ultrasonic velocity was measured at 25° C. using a sing-around acoustic velocity measurement apparatus (trade name: "UVM-2 model", manufactured by Ultrasonic Engineering Co., Ltd.) according to JIS Z2353 (2003). For each sheet, the entire inside of three circular regions having a diameter of 1.5 cm (small probe size of a single channel) was used as the acoustic velocity measurement target.

<Density>
A 10 mm×10 mm test piece was cut out from the above acoustic velocity measurement target (circle with a diameter of 1.5 cm). The density of the test piece at 25° C. was measured using an electronic hydrometer (trade name: "SD-200L", manufactured by Alfa Mirage Co., Ltd.) in accordance with the density measurement method of Method A (underwater substitution method) described in JIS K7112 (1999).

-Evaluation Standards-
A: The acoustic impedance is less than 0.5 Mrayl
B: The acoustic impedance is 0.5 Mrayl or more and less than 0.7 Mrayl
C: The acoustic impedance is 0.7 Mrayl or more

TABLE 1

| | Epoxy resin and curing agent | | | | | | Metal particle | | Ceramic particle | | | | | |
| --- | --- | --- | --- | --- | --- | --- | --- | --- | --- | --- | --- | --- | --- | --- |
| | Type | Parts by mass | Curing agent | Parts by mass | Catalyst | Parts by mass | Type | Parts by mass | Type | Parts by mass | Acoustic velocity [m/sec] | AI [Mrayl] | Variation in AI | Manufacturing method |
| Example 1 | C-1 | 4 | D-1 | 1 | — | — | Fe | 90 | Cordierite | 5 | C | B | A | Planetary centrifugal mixer |
| Example 2 | C-1 | 4 | D-1 | 1 | — | — | Co | 90 | Cordierite | 5 | C | B | A | Planetary centrifugal mixer |
| Example 3 | C-1 | 8 | D-1 | 2 | — | — | Zr | 85 | Cordierite | 5 | B | B | A | Planetary centrifugal mixer |
| Example 4 | C-1 | 4 | D-1 | 1 | — | — | Mo | 90 | Cordierite | 5 | B | B | A | Planetary centrifugal mixer |
| Example 5 | C-1 | 4 | D-1 | 1 | — | — | WC | 90 | Cordierite | 5 | B | A | A | Planetary centrifugal mixer |
| Example 6 | C-1 | 4 | D-1 | 1 | — | — | WC | 85 | Cordierite | 10 | A | B | A | Planetary centrifugal mixer |
| Example 7 | C-1 | 4 | D-1 | 1 | — | — | WC | 80 | Cordierite | 15 | C | B | A | Planetary centrifugal mixer |
| Example 8 | C-1 | 8 | D-1 | 2 | — | — | WC | 85 | Cordierite | 5 | A | B | A | Planetary centrifugal mixer |
| Example 9 | C-1 | 4 | D-1 | 1 | — | — | W | 90 | Cordierite | 5 | B | A | A | Planetary centrifugal mixer |
| Example 10 | C-1 | 4 | D-1 | 1 | — | — | W | 85 | Cordierite | 10 | A | B | A | Planetary centrifugal mixer |

TABLE 1-continued

| | Epoxy resin and curing agent | | | | | | Metal particle | | Ceramic particle | | Acoustic velocity [m/sec] | AI [Mrayl] | Variation in AI | Manufacturing method |
|---|---|---|---|---|---|---|---|---|---|---|---|---|---|---|
| | Type | Parts by mass | Curing agent | Parts by mass | Catalyst | Parts by mass | Type | Parts by mass | Type | Parts by mass | | | | |
| Example 11 | C-1 | 4 | D-1 | 1 | — | — | W | 80 | Cordierite | 15 | C | B | B | Planetary centrifugal mixer |
| Example 12 | C-2 | 4.1 | D-1 | 0.9 | — | — | WC | 90 | Cordierite | 5 | A | A | A | Planetary centrifugal mixer |
| Example 13 | C-3 | 4.2 | D-1 | 0.8 | — | — | WC | 90 | Cordierite | 5 | A | A | A | Planetary centrifugal mixer |
| Example 14 | C-4 | 4 | D-1 | 1 | — | — | WC | 90 | Cordierite | 5 | A | A | A | Planetary centrifugal mixer |
| Example 15 | C-5 | 4.2 | D-1 | 0.8 | — | — | WC | 90 | Cordierite | 5 | A | B | A | Planetary centrifugal mixer |
| Example 16 | C-6 | 3.6 | D-1 | 1.4 | — | — | WC | 90 | Cordierite | 5 | A | A | A | Planetary centrifugal mixer |
| Example 17 | C-7 | 4 | D-1 | 1 | — | — | WC | 90 | Cordierite | 5 | A | A | B | Planetary centrifugal mixer |
| Example 18 | C-1 | 4.9 | D-2 | 0.1 | — | — | WC | 90 | Cordierite | 5 | A | A | A | Planetary centrifugal mixer |
| Example 19 | C-1 | 4.9 | D-3 | 0.1 | — | — | WC | 90 | Cordierite | 5 | A | A | A | Planetary centrifugal mixer |
| Example 20 | C-1 | 4.9 | D-4 | 0.1 | — | — | WC | 90 | Cordierite | 5 | A | A | A | Planetary centrifugal mixer |
| Example 21 | C-1 | 4 | D-5 | 1 | — | — | WC | 90 | Cordierite | 5 | A | A | A | Planetary centrifugal mixer |
| Example 22 | C-1 | 4.3 | D-6 | 0.7 | — | — | WC | 90 | Cordierite | 5 | A | A | A | Planetary centrifugal mixer |
| Example 23 | C-1 | 3.5 | D-7 | 1.5 | — | — | WC | 90 | Cordierite | 5 | A | B | A | Planetary centrifugal mixer |
| Example 24 | C-1 | 4.9 | D-8 | 0.1 | — | — | WC | 90 | Cordierite | 5 | A | A | B | Planetary centrifugal mixer |
| Example 25 | C-1 | 4 | D-9 | 1 | — | — | WC | 90 | Cordierite | 5 | A | B | B | Planetary centrifugal mixer |
| Example 26 | C-1 | 4.8 | — | — | E-1 | 0.2 | WC | 90 | Cordierite | 5 | B | B | B | Planetary centrifugal mixer |
| Example 27 | C-1 | 4 | D-1 | 1 | — | — | WC | 90 | Spinel | 5 | C | A | B | Planetary centrifugal mixer |
| Example 28 | C-1 | 4 | D-1 | 1 | — | — | WC | 90 | Wollastonite | 5 | C | A | B | Planetary centrifugal mixer |
| Example 29 | C-1 | 4 | D-1 | 1 | — | — | WC | 90 | $B_4C$ | 5 | B | A | A | Planetary centrifugal mixer |
| Example 30 | C-1 | 4 | D-1 | 1 | — | — | WC | 90 | SiC | 5 | B | A | A | Planetary centrifugal mixer |
| Example 31 | C-1 | 4 | D-1 | 1 | — | — | WC | 90 | $Al_2O_3$ | 5 | B | A | A | Planetary centrifugal mixer |
| Example 32 | C-1 | 4 | D-1 | 1 | — | — | WC | 90 | AlN | 5 | B | A | A | Planetary centrifugal mixer |
| Example 33 | C-1 | 4 | D-1 | 1 | — | — | WC | 90 | MgO | 5 | A | A | A | Planetary centrifugal mixer |
| Example 34 | C-1 | 4 | D-1 | 1 | — | — | WC | 90 | $Si_3N_4$ | 5 | B | A | A | Planetary centrifugal mixer |
| Example 35 | C-1 | 4 | D-1 | 1 | — | — | WC | 90 | BN | 5 | B | A | A | Planetary centrifugal mixer |
| Example 36 | C-1 | 4 | D-1 | 1 | — | — | WC | 90 | $Y_2O_3$ | 5 | A | A | B | Planetary centrifugal mixer |
| Comparative Example 1 | C-1 | 4 | D-1 | 1 | — | — | WC | 95 | — | — | A | B | C | Planetary centrifugal mixer |
| Comparative Example 2 | C-1 | 4 | D-1 | 1 | — | — | W | 95 | — | — | A | A | C | Planetary centrifugal mixer |
| Comparative Example 3 | C-1 | 12 | D-1 | 3 | — | — | W | 85 | — | — | A | D | C | Planetary centrifugal mixer |
| Comparative Example 4 | C-1 | 4 | D-1 | 1 | — | — | Mo | 95 | — | — | A | B | C | Planetary centrifugal mixer |
| Comparative Example 5 | C-1 | 16 | D-1 | 4 | — | — | — | — | Cordierite | 80 | B | D | A | Planetary centrifugal mixer |
| Comparative Example 6 | C-1 | 16 | D-1 | 4 | — | — | — | — | $B_4C$ | 80 | D | D | A | Planetary centrifugal mixer |
| Comparative Example 7 | C-1 | 16 | D-1 | 4 | — | — | — | — | SiC | 80 | C | D | A | Planetary centrifugal mixer |
| Comparative Example 8 | C-1 | 16 | D-1 | 4 | — | — | — | — | AlN | 80 | C | D | A | Planetary centrifugal mixer |
| Comparative Example 9 | C-1 | 16 | D-1 | 4 | — | — | — | — | $Si_3N_4$ | 80 | C | D | A | Planetary centrifugal mixer |

TABLE 1-continued

| | Epoxy resin and curing agent | | | | Catalyst | Parts by mass | Metal particle Type | Parts by mass | Ceramic particle Type | Parts by mass | Acoustic velocity [m/sec] | AI [Mrayl] | Variation in AI | Manufacturing method |
|---|---|---|---|---|---|---|---|---|---|---|---|---|---|---|
| | Type | Parts by mass | Curing agent | Parts by mass | | | | | | | | | | |
| Comparative Example 10 | C-1 | 16 | D-1 | 4 | — | — | — | — | BN | 80 | D | D | A | Planetary centrifugal mixer |
| Comparative Example 11 | C-1 | 4 | D-1 | 1 | — | — | WC | 90 | Cordierite | 5 | Materials could not be mixed | | | Kneader |
| Comparative Example 12 | C-1 | 4 | D-1 | 1 | — | — | WC | 90 | Cordierite | 5 | Materials could not be mixed | | | Pressurized kneader |
| Comparative Example 13 | C-1 | 4 | D-1 | 1 | — | — | WC | 90 | Cordierite | 5 | Materials could not be mixed | | | Banbuly mixer |
| Comparative Example 14 | C-1 | 4 | D-1 | 1 | — | — | WC | 90 | Cordierite | 5 | Accurate evaluation not possible due to heterogeneity of cured substance | | | Three roll mill |

<Notes of tables>
" ": it means that the corresponding component is not contained.
[Epoxy resin]
(C-1) bisphenol A diglycidyl ether ("jER825", trade name, manufactured by Mitsubishi Chemical Corporation, epoxy equivalent: 170)
(C-2) bisphenol A diglycidyl ether ("jER828", trade name, manufactured by Mitsubishi Chemical Corporation, epoxy equivalent: 190)
(C-3) bisphenol A diglycidyl ether ("jER834", trade name, manufactured by Mitsubishi Chemical Corporation, epoxy equivalent: 230)
(C-4) bisphenol F diglycidyl ether ("EPICLON 830", trade name, manufactured by DIC Corporation, epoxy equivalent: 170)
(C-5) bisphenol A propoxylate diglycidyl ether (manufactured by Sigma-Aldrich Co. LLC, epoxy equivalent: 228)
(C-6) 4,4'-methylenebis(N,N-diglycidylaniline)(manufactured by Tokyo Chemical Industry Co., Ltd., epoxy equivalent: 106)
(C-7) poly [(phenylglycidyl ether)-co-formaldehyde] (manufactured by Sigma-Aldrich Co. LLC, epoxy equivalent: 172)
[Curing agent]
(D-1) isophorone diamine (manufactured by FUJIFILM Wako Pure Chemical Corporation)
(D-2) triethylenetetramine (manufactured by Tokyo Chemical Industry Co., Ltd.)
(D-3) 2,4,6-tris(dimethylaminomethyl)phenol (trade name: "LUVEAK DMP-30", manufactured by Nacalai Tesque Inc.)
(D-4) polyamide amine (trade name: "LUCKAMIDE EA-330", manufactured by DIC Corporation)
(D-5) mensen diamine (manufactured by Sigma-Aldrich Co. LLC)
(D-6) m-phenylenediamine (manufactured by FUJIFILM Wako Pure Chemical Corporation)
(D-7) polyetheramine T-403 (trade name, manufactured by BASF SE)
(D-8) 2-ethyl-4-methylimidazole (manufactured by Tokyo Chemical Industry Co., Ltd.)
(D-9) hexahydrophthalic anhydride (trade name: "RIKACID HH", manufactured by New Japan Chemical Co., Ltd.)
[Catalyst]
(E-1) 2,4,6-tris(dimethylaminomethyl)phenol (trade name: "LUVEAK DMP-30", manufactured by Nacalai Tesque Inc.)
[Metal particle]
Fe: EW-I (particle diameter: 2 μm, specific gravity: 7.9, manufactured by BASF SE)
Co: cobalt powder S-series (particle diameter: 4 μm, specific gravity: 8.9, manufactured by Jervois Finland Oy)
Zr: RC-100 zirconium oxide (particle diameter: 1 to 4 μm, specific gravity: 5.7, manufactured by Daiichi Kigenso Kagaku Kogyo Co., Ltd.)
Mo: molybdenum powder Mo-6 (particle diameter: 6 μm, specific gravity: 10.3, trade name, manufactured by Japan New Metals Co., Ltd.)
WC: Uniform particle tungsten carbide powder (particle diameter: 9 μm, specific gravity: 15.6, manufactured by A.L.M.T. Corp.)
W: Uniform particle tungsten powder (particle diameter: 5 μm, specific gravity: 19.3) (manufactured by A.L.M.T. Corp.)
[Ceramic particle]
Cordierite: synthetic cordierite fine particle product SS-400 (particle diameter: 4.5 μm, trade name, manufactured by Marusu Glaze Co., Ltd.)
Spinel: TATEMIC SN-1 form (particle diameter: 3 μm, trade name, manufactured by Tateho Chemical Industries Co., Ltd.)
Wollastonite: KGP-H40 (particle diameter: 4 μm, trade name, manufactured by Maruto Co., Ltd.)
$B_4C$: boron carbide powder F1000 (particle diameter: 1 to 10 μm, trade name, manufactured by ESK Ceramics GmbH & Co. KG)
SiC: SiC powder β-SiC1200 (particle diameter: 6 μm, trade name, manufactured by Superior Graphite Co., Ltd.)
$Al_2O_3$: DAM-03 (particle diameter: 8 μm, trade name, manufactured by Denka Company Limited)
AN: aluminum nitride FAN-f05-A1 (particle diameter: 4 μm, trade name, manufactured by Matsuo Sangyo Co., Ltd.)
MgO: SMO-5 (particle diameter: 5 μm, manufactured by Sakai Chemical Industry Co., Ltd.)
$Si_3N_4$: UBE silicon nitride high-purity product SN-XLF (particle diameter: 2 μm, trade name, manufactured by Ube Industries, Ltd.)
BN: Denka boron nitride powder HGP (particle diameter: 5 μm, trade name, manufactured by Denka Company Limited)
$Y_2O_3$: standard product 3N (particle diameter: 4 μm, trade name, manufactured by Nippon Yttrium Co., Ltd.)

As is clear from Table 1, it can be seen that the acoustic matching sheet according to the embodiment of the present invention exhibits an appropriate acoustic velocity, can achieve both thinning of an acoustic matching layer and improvement of acoustic impedance, and also has little variation in acoustic wave characteristics within the layer.

EXPLANATION OF REFERENCES

1: acoustic lens
2: acoustic matching layer
3: piezoelectric element layer
4: backing material
7: housing
9: cord
10: ultrasound probe

What is claimed is:
1. An acoustic wave probe comprising:
   an acoustic matching sheet, the acoustic matching sheet comprising an acoustic matching layer material,
   wherein the acoustic matching layer material comprises:
   an epoxy resin component;
   a metal particle; and
   a ceramic particle, and
   wherein the acoustic matching layer material has an acoustic velocity of less than 3,500 m/sec and an acoustic impedance of 18 Mrayl or more.
2. The acoustic wave probe according to claim 1, wherein the acoustic matching layer material further comprises a curing agent component.

3. The acoustic wave probe according to claim 1,
wherein the epoxy resin component contains at least one of a bisphenol A type epoxy resin component or a bisphenol F type epoxy resin component.

4. The acoustic wave probe according to claim 2,
wherein the curing agent component contains at least one of a primary amine component or a secondary amine component.

5. The acoustic wave probe according to claim 1,
wherein the metal particle contains at least one metal of Groups 4 to 12 of the periodic table.

6. The acoustic wave probe according to claim 1,
wherein the metal particle has a specific gravity of 9 or more.

7. The acoustic wave probe according to claim 1,
wherein the ceramic particle contains at least one atom of Groups 1 to 3 or 13 to 17 of the periodic table.

8. The acoustic wave probe according to claim 1,
wherein the ceramic particle contains at least one of Mg, Ca, Ba, B, Al, Y, or Si and at least one of O, C, N, or S.

9. The acoustic wave probe according to claim 1,
wherein the ceramic particle contains at least one of cordierite, boron carbide, silicon carbide, alumina, aluminum nitride, magnesium oxide, silicon nitride, boron nitride, or yttrium oxide.

10. An acoustic wave measurement apparatus comprising the acoustic wave probe according to claim 1.

11. The acoustic wave measurement apparatus according to claim 10,
wherein the acoustic wave measurement apparatus is an ultrasound diagnostic apparatus.

\* \* \* \* \*